US005482936A

United States Patent [19]

Lindstrom

[11] Patent Number: 5,482,936

[45] Date of Patent: Jan. 9, 1996

[54] IMIDAZO[4,5-C]QUINOLINE AMINES

[75] Inventor: Kyle J. Lindstrom, Houlton, Wis.

[73] Assignee: Minnesota Mining and Manufacturing Company, St. Paul, Minn.

[21] Appl. No.: 371,845

[22] Filed: Jan. 12, 1995

[51] Int. Cl.$^6$ ...................... C07D 471/14; C07D 498/14; A61K 31/47; A61K 31/535

[52] U.S. Cl. .......................... 514/183; 514/211; 514/214; 514/219; 514/224.5; 514/229.5; 514/248; 514/257; 514/287; 540/468; 540/471; 540/476; 540/546; 540/555; 540/578; 544/14; 544/95; 544/99; 544/247; 544/343; 546/64

[58] Field of Search .................................... 540/468, 471, 540/476, 546, 555, 578; 544/14, 95, 99, 247, 343; 546/64; 514/183, 211, 214, 219, 224.5, 229.5, 248, 257, 287

[56] References Cited

U.S. PATENT DOCUMENTS

| | | | |
|---|---|---|---|
| 4,689,338 | 8/1987 | Gerster | 514/293 |
| 4,929,624 | 5/1990 | Gerster et al. | 514/293 |
| 5,037,986 | 8/1991 | Gerster | 546/82 |
| 5,266,575 | 11/1993 | Gerster et al. | 514/293 |
| 5,268,376 | 12/1993 | Gerster | 514/293 |
| 5,346,905 | 9/1994 | Gerster | 514/293 |
| 5,352,784 | 10/1994 | Nikolaides et al. | 594/126 |

FOREIGN PATENT DOCUMENTS

| | | |
|---|---|---|
| 385630A2 | 9/1990 | European Pat. Off. . |
| 92/15582 | 9/1992 | WIPO . |

*Primary Examiner*—Philip I. Datlow
*Attorney, Agent, or Firm*—Gary L. Griswold; Walter N. Kirn; Robert H. Brink

[57] ABSTRACT

Compounds and pharmaceutically acceptable salts thereof formally derived by bridging the 1- and 2-positions of 1H-imidazo[4,5-c]quinolin-4-amines. Also, methods of using such compounds and pharmaceutical formulations containing such compounds. Said compounds are useful to induce interferon biosynthesis in an animal.

12 Claims, No Drawings

IMIDAZO[ 4,5-C] QUINOLINE AMINES

BACKGROUND OF THE INVENTION

1. Field of the Invention

This invention relates to imidazo[4,5-c]quinoline amine compounds. In another aspect this invention relates to immunomodulator compounds. In other aspects this invention relates to pharmaceutical compositions containing such compounds, and pharmacological methods of using such compounds.

2. Description of the Related Art

Certain 1H-imidazo[4,5-c]quinolin-4-amines are known as antiviral agents and/or as immunomodulators. Such compounds are disclosed e.g., in U.S. Pat. Nos. 4,689,338, 4,929,624, 5,037,986, 5,266,575, 5,268,376, 5,346,905, European Patent Application No. 0,385,630 A2 and WO92/15582 (all to Gerster et al.). Commonly assigned copending application 08/092,002 (Lindstrom et al.) filed Jul. 15, 1993, now abandoned, discloses immunomodulator imidazopyridine amines of the formula

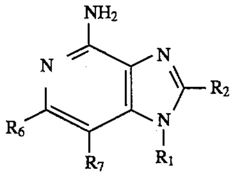

$R_1$ is selected from the group consisting of hydrogen; $CHR_xR_y$ wherein $R_x$ is hydrogen and $R_y$ is selected from the group consisting of straight chain, branched chain, or cyclic alkyl containing one to about ten carbon atoms, straight chain or branched chain alkenyl containing two to about ten carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, and phenylethyl; and $—CH{=}CR_zR_z$ wherein each $R_z$ is independently straight chain, branched chain, or cyclic alkyl of one to about six carbon atoms.

U.S. Pat. No. 5,352,784 (Nickolaides et al.) discloses immunomodulator 6,7-fused cycloalkylimidazopyridine amines.

SUMMARY OF THE INVENTION

1H-Imidazo[4,5-c]quinolin-4-amines are compounds of the general skeletal Formula I, having the numbering system shown:

I

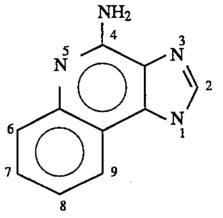

This invention provides compounds and pharmaceutically acceptable salts thereof formally derived by bridging the 1- and 2-positions of 1H-imidazo[4,5-c]quinolin-4-amines. In particular this invention provides compounds of Formula II

II

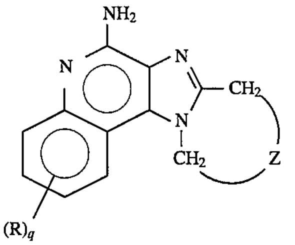

wherein R, Z, and q are as defined in detail below, and pharmaceutically acceptable salts thereof.

This invention also provides a pharmaceutical formulation comprising: (i) a compound of Formula II in an amount effective to induce interferon biosynthesis in an animal, and (ii) a pharmaceutically acceptable carrier. This invention further provides a method of inducing interferon biosynthesis in an animal, comprising the step of administering to said animal a compound of Formula II in an amount effective to induce said interferon biosynthesis.

DETAILED DESCRIPTION OF THE INVENTION

This invention provides compounds of Formula II wherein Z is selected from the group consisting of:

$—(CH_2)_n—$ wherein n is 1 to 4, $—(CH_2)_a—C(R_1R_2)(CH_2)_b—$, wherein a and b are integers and a+b is 0 to 3, $R_1$ is hydrogen or alkyl of 1 to 4 carbon atoms, and $R_2$ is selected from the group consisting of alkyl of 1 to 4 carbon atoms, hydroxy, $—OR_3$ wherein $R_3$ is alkyl of 1 to 4 carbon atoms, and $—NR_4R'_4$ wherein $R_4$ and $R'_4$ are independently hydrogen or alkyl of 1 to 4 carbon atoms, $—(CH_2)_a—(Y)—(CH_2)_b—$ wherein a and b are integers and a+b is 0 to 3, and Y is O, S, or $—NR_5—$ wherein $R_5$ is hydrogen or alkyl of 1 to 4 carbon atoms, and wherein q is 0 or 1 and R is selected from the group consisting of alkyl of 1 to 4 carbon atoms, alkoxy of 1 to 4 carbon atoms, and halogen, and pharmaceutically acceptable salts thereof.

When Z is $—(CH_2)_n—$ as defined above it is preferably alkylene having 1, 2, or 3 carbon atoms. When Z is $—(CH_2)_a—C(R_1R_2)(CH_2)_b—$ as defined above $R_1$ is preferably hydrogen and $R_2$ is preferably alkyl of 1 to 4 carbon atoms, most preferably methyl. When Z is $—(CH_2)_a—(Y)—(CH_2)_b—$ as defined above Y is preferably O, and when Y is O a+b is preferably 1.

Preferred compounds of the invention include:

8,9,10,11-tetrahydropyrido[1',2',:1,2] imidazo[4,5-c]quinolin-6-amine, i.e.,

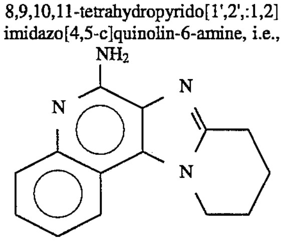

10-methyl-8,9,10,11-tetrahydropyrido[1',2',:1,2] imidazo[4,5-c]quinolin-6-amine, i.e., -continued

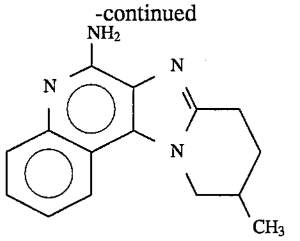

8H-9,10,11,12-tetrahydrohexamethyleneimino[1',2':1,2] imidazo[4,5-c]quinolin-6-amine, i.e.,

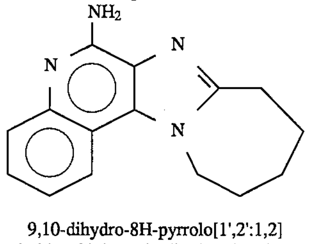

9,10-dihydro-8H-pyrrolo[1',2':1,2] imidazo[4,5-c]quinolin-4-amine, i.e.,

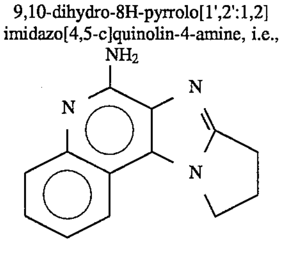

and 10,11-dihydro-8H-[1,4]-oxazino[4', 3':1,2] imidazo[4,5-c]quinolin-6-amine, i.e.,

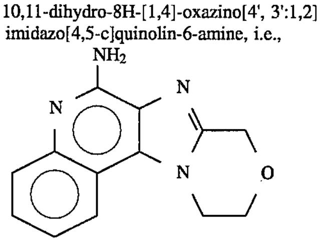

Reaction Scheme I illustrates preparation of the compounds of the invention. The unsubstituted compound of Formula XI is a known commercially available compound and other compounds of Formula XI can be prepared by methods known to those skilled in the art and disclosed, e.g., in *Chem. Ber.* 1927, 60, 1108 (Kohler) and *J. Heterocyclic Chem.* 1988, 25, 857 (Kappe).

In step (i) a 3-nitroquinoline-2,4-disulfonate is first prepared by reacting a 2,4-dihydroxy-3-nitroquinoline with a sulfonyl halide or preferably a sulfonic anhydride. Suitable sulfonyl halides include alkylsulfonyl halides such as methanesulfonyl chloride and trifluoromethanesulfonyl chloride, and arylsulfonyl halides such as benzenesulfonyl chloride, p-bromobenzenesulfonyl chloride, and p-toluenesulfonyl chloride. Suitable sulfonic anhydrides include those corresponding to the above-mentioned sulfonyl halides. A particularly preferred sulfonic anhydride is trifluoromethanesulfonic anhydride.

Reaction conditions preferably involve first combining a compound of Formula XI with a base, preferably an excess of a tertiary amine base (e.g., a trialkylamine base such as triethylamine) and preferably in an appropriate solvent such as dichloromethane and then adding the sulfonyl halide or the sulfonic anhydride. The addition is preferably carried out in a controlled fashion (e.g., dropwise) and at a reduced temperature (e.g., at about 0° C.).

REACTION SCHEME I

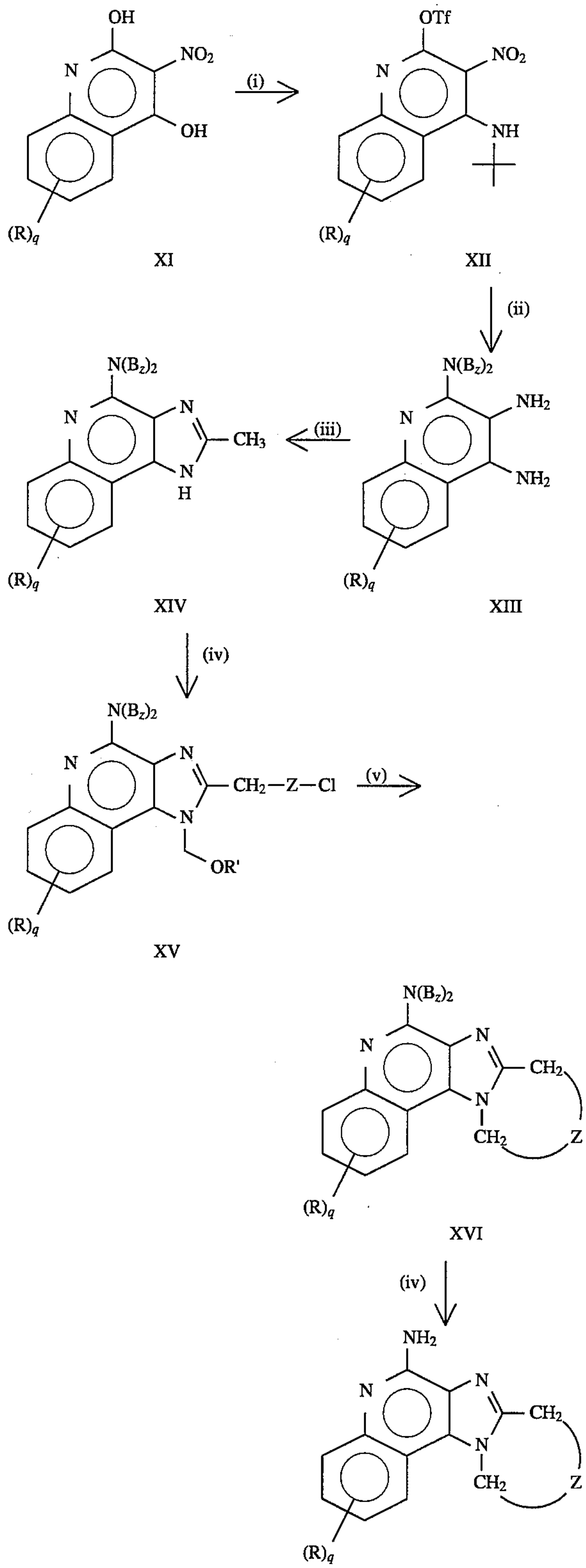

XI XII XIII XIV XV XVI II

The disulfonate is then reacted with tert-butylamine, preferably in the presence of an excess of a tertiary amine base in a solvent such as dichloromethane to afford a compound of Formula XII. The reaction can be carried out by adding the tertiary amine base to the reaction mixture resulting from the first porion of step (i), cooling to a reduced temperature (e.g., 0° C.) and adding the tert-butylamine in a controlled fashion (e.g., dropwise). The reaction can also be carried out by adding the tert-butylamine to a solution of the disulfonate and a tertiary amine base in a solvent such as dichloromethane. The reaction can be run at relatively low temperatures, e.g., about 0° C., in order to decrease the amount of undesired 2-aminated and 2,4-diaminated side products. It is sometimes necessary or desirable to heat the reaction mixture after the addition in order to complete the reaction.

In step (ii) the compound of Formula XII is reacted with dibenzylamine. The reaction can be carried out by placing the starting material and the dibenzylamine in an inert solvent such as benzene, toluene, or xylene, and heating at a temperature and for a time sufficient to cause displacement of the sulfonate group by the dibenzylamine, such temperature and time being readily selected by those skilled in the art. The tert-butyl group is then removed by heating in a polar solvent: such as methanol in the presence of an acid such as hydrochloric acid.

The nitro group is then reduced to an amino group. Methods for such a reduction are well known to those skilled in the art:. A preferred method involves in situ generation of $Ni_2B$ from sodium borohydride and $NiCl_2$ in methanol to afford a reducing agent solution. The nitro compound is added to the reducing agent solution to effect reduction of the nitro group. The product is a compound of Formula XIII.

In step (iii) a compound of Formula XIII is reacted with acetic acid or an equivalent thereof to afford the cyclized compound of Formula XIV. Suitable equivalents to acetic acid include corresponding acetyl halides and orthoesters. When using acetic acid or an orthoester equivalent the reaction can be run in the absence of solvent or in an inert solvent such as xylene or toluene with sufficient heating (e.g., at about 80°–150° C. depending on the solvent if any) to drive off any alcohol or water formed as a side product of the reaction. When using an acetyl halide the reaction is preferably run in acetic acid with heating.

In step (iv) the cyclized compound of Formula XIV is first substituted at the 1-position with an alkoxymethyl group ($—CH_2OR'$ wherein R' is alkyl such as ethyl) in order to protect the 1-nitrogen. The substitution can be carried out by treating the compound of Formula XIV with sodium hydride and a halomethylalkyl ether such as chloromethyl ethyl ether. The resulting 1-protected compound is then substituted on the 2-methyl group with a moiety of the formula —ZCl to afford a compound of Formula XV. This can be accomplished by metalating the 2-methyl group of the 1-protected compound, e.g., by treating with n-butyl lithium in tetrahydrofuran, then adding an alkylating agent of the formula X'—ZCl wherein X' is a more facile leaving group than chloro (e.g., X' can be bromo). Another suitable method of substituting on the 2-methyl group involves metalating, reacting with an epoxide such as ethylene oxide, and converting the resulting 2-(hydroxyalkyl) compound to the corresponding halide by reacting with a chlorinating agent such as thionyl chloride in an inert solvent.

In step (v) the 1-position of a compound of Formula XV is deprotected, e.g., by heating in the presence of HCl in a solvent such as methanol. The resulting 1-hydrogen compound is then cyclized by formal displacement of the chloro group by the 1-nitrogen. Treating with sodium iodide in a polar solvent such as acetone in the presence of a neutralizing base (e.g., potassium carbonate) is a suitable means for affecting cyclization. A compound of Formula XVI results.

In step (vi) the compound of Formula XVI is hydrogenolyzed to afford the corresponding 4-amino compound of Formula II. Conventional well known catalytic hydrogenation conditions are suitable. Preferred conditions involve heating in formic acid in the presence of $Pd(OH)_2/C$.

Reaction Scheme II shows a route to certain compounds of the invention not amenable to preparation via Reaction Scheme I.

REACTION SCHEME II

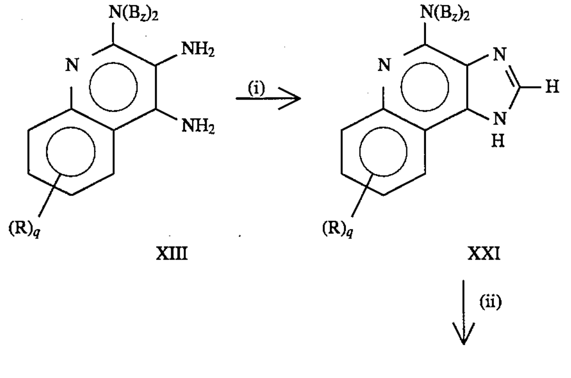

XIII

XXI

-continued
REACTION SCHEME II

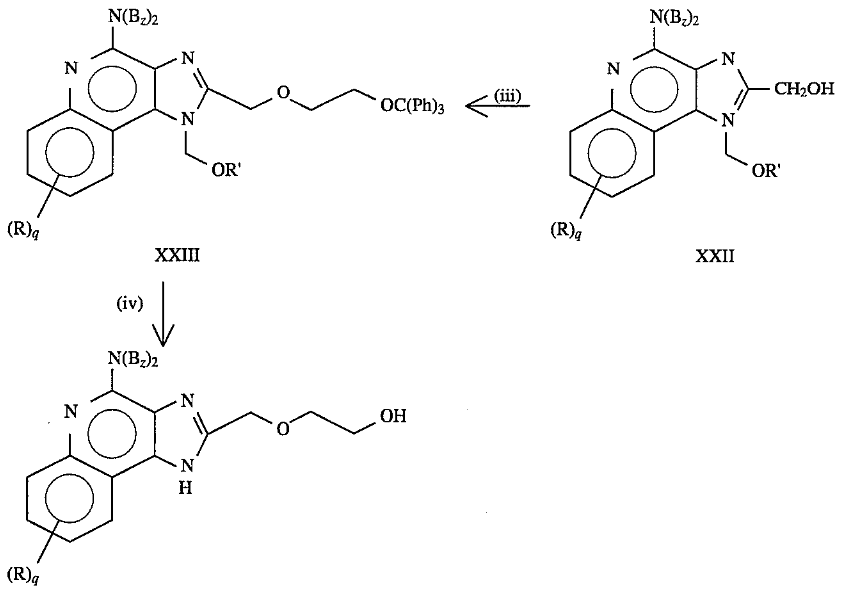

XXIII XXII XXIV

In step (i) a compound of Formula XIII is cyclized using formic acid or an equivalent thereof such as an orthoformate (e.g., triethylorthoformate) to provide a compound of Formula XXI (see, e.g., step (iii) of Reaction Scheme I). In step (ii) the compound of Formula XXI is protected at the 1-position as described above in connection with step (iv) of Reaction Scheme I. The protected product is then formylated at the 2-position by first metalating in a polar solvent such as tetrahydrofuran, e.g., reacting with n-butyllithium, and then treating with formaldehyde. Step (iii) involves homologating the 2-substituent of the compound of Formula XXII, e.g., by reacting with 1-bromo-2-(triphenylmethoxy)ethane. The product of Formula XXIII can be carried on to a compound of Formula II by acid catalyzed hydrolysis of the protecting groups to afford a compound of Formula XXIV, conversion of the hydroxyl group on the 2-substituent to an appropriate leaving group, cyclization (e.g., as described above in connection with step (v) of Reaction Scheme I), and reductive cleavage as described above in connection with step (vi) of Reaction Scheme I.

Compounds of Formula II not amenable to being prepared via the routes illustrated in Reaction Schemes I or II, or otherwise described herein can be prepared using variants of the illustrated schemes involving well known synthetic alternatives, alteration of the order of steps, and the like.

The product compound of Formula II can be isolated by the conventional means disclosed in U.S. Pat. No. 4,689,338 (Gerster), such as, for example, removal of the solvent and recrystallization from an appropriate solvent (e.g., N,N-dimethylformamide) or solvent mixture, or by dissolution in an appropriate solvent (such as methanol) and re-precipitation by addition of a second solvent in which the compound is insoluble.

A compound of Formula II can be used as an antiviral agent itself or it can be used in the form of a pharmaceutically acceptable salt such as a hydrochloride, dihydrogen sulfate, trihydrogen phosphate, hydrogen nitrate, methanesulfonate or a salt of another pharmaceutically acceptable acid. A pharmaceutically acceptable salt of a compound of Formula II can be readily prepared, generally by reaction of the compound with an equimolar amount of a relatively strong acid, preferably an inorganic acid such as hydrochloric, sulfuric, or phosphoric acid, or an organic acid such as methanesulfonic acid, in a polar solvent. Isolation of the salt is facilitated by the addition of a solvent, such as diethyl ether, in which the salt is insoluble.

A compound of the invention can be formulated for the various routes of administration (e.g., oral administration by tablet, capsule, oral suspension, or the like, topical, transdermal, or parenteral) by combining a therapeutically effective amount of a compound of Formula II with an appropriate pharmaceutically acceptable vehicle including any adjuvants and excipients suitable for the selected dosage form. Suitable formulations include parenteral solutions, topical creams, gels, and ointments, and oral tablets and capsules. Methods of manufacture of such pharmaceutical compositions are well known to those skilled in the art and disclosed, e.g., in *Remington's Pharmaceutical Sciences,* 18th Edition, 1990 Mack Publishing Company, A. R. Gennaro, Editor. Consequently, particular formulations suitable for a selected route of administration can be readily identified and prepared by those skilled in the art. A solid dosage form, for example, contains a compound of Formula II, and one or more diluents (e.g., dicalcium phosphate, calcium sulfate, lactose, mannitol, cellulose, kaolin, sodium chloride, starch, sucrose, inositol, sorbitol), binders (e.g., starch, gelatin, sucrose, glucose, dextrose, molasses, lactose, natural and synthetic gums), lubricants (e.g., talc, magnesium stearate, calcium stearate, stearic acid, hydrogenated vegetable oils, polyethylene glycols), disintegrants (e.g., corn starch, potato starch, clays, cellulose, alginates), coloring agents, and flavoring agents. A parenteral solution contains a compound of Formula II and a pharmaceutically acceptable aqueous vehicle including suitable excipients, such as acids (hydrochloric acid, lactic acid, acetic acid, aspartic acid or mixtures thereof) or bases (sodium hydroxide) sufficient to achieve a pH of 2 to about 6, and tonicity adjusters (e.g., sorbitol or glycerin) in order that the formulation is isotonic with serum. Topical or transdermal formulations contain a compound of Formula II in a cream, ointment, or a pressure sensitive adhesive composition. A cream can contain emollients (e.g., cetyl alcohol, stearyl alcohol, petrolatum, light mineral oil, acetylated lanolin), emulsifiers (e.g., nonionic surfactants such as polysorbate 60, sorbitan monostearate), thickeners (e.g., montmorillonite clays or long chain alcohols such as cetearyl alcohol, cetyl alcohol, and stearyl alcohol), and preservatives (e.g., methylparaben, propylparaben, benzyl alcohol) in amounts readily selected by those skilled in the art. An ointment contains an ointment base (e.g., polyethylene glycol, petrolatum) and emollients and thickeners.

The amount of compound of Formula II that constitutes a therapeutically effective amount will vary according to the particular compound used, the desired therapeutic effect, the condition being treated, the dosing regimen, and the route of administration. Generally, a compound of Formula II will be present in a parenteral formulation in an amount of about 0.1 to about 10 percent by weight based on the total weight of the formulation. Similarly an oral tablet or capsule will generally contain about 0.5 to about 50 percent by weight; and a topical or transdermal formulation will contain about 0.1 to about 10 percent by weight. Particular formulations will be easily selected by those skilled in the art.

A number of compounds of Formula II were tested and found to induce biosynthesis of interferon in human cells and in mice. These results suggest that at least certain compounds of the invention might be useful in treating viral diseases (e.g., hepatitis, herpes, warts) and diseases such as rheumatoid arthritis, eczema, psoriasis, multiple sclerosis, essential thrombocythaemia, cancer such as basal cell carcinoma, and other neoplastic diseases.

The examples below are intended to illustrate the invention. The structures were confirmed by nuclear magnetic resonance spectroscopy.

EXAMPLE 1

8,9,10,11-Tetrahydropyrido[1',2':1,2[imidazo[4,5-c]quinolin-6-amine

Part A

Triethylamine (84 mL, 0.6 mole) was added to a suspension of 3-nitro-2,4-quinolinediol (40 g, 0.194 mole) in methylene chloride (1200 mL). The resulting solution was cooled in an ice bath and trifluoromethanesulfonic anhydride (67.2 mL, 0.40 mole) was added. After the addition was complete, the reaction was heated on a steam bath for 10 minutes then once again cooled in an ice bath. Tert-butylamine (42 mL, 0.4 mole) was added then the reaction was heated on a steam bath for 15 minutes. The reaction mixture was washed with aqueous sodium bicarbonate (500 mL), dried over magnesium sulfate then concentrated under vacuum. The concentrate was put through a layer of silica gel and the silica gel was eluted with methylene chloride. The methylene chloride solution was evaporated under vacuum to provide 54 g of [4-(1,1-dimethylethyl)amino-3-nitroquinolin-2-yl]trifluoromethanesulfonate.

Part B

Triethylamine (19.2 mL, 0.137 mole) was added to a solution of [4-(1,1-dimethylethyl)amino-3-nitroquinolin-2-yl]trifluoromethanesulfonate (54 g, 0.137 mole) in toluene (about 1 L). Dibenzylamine (27 mL, 0.137 mole) was added and the reaction mixture was heated at reflux for about 2 hours. The reaction mixture was concentrated under vacuum. The residue was diluted with methanol (900 mL). Hydrochloric acid (100 mL of 6N) was added and the reaction mixture was heated at reflux for 1 hour. The reaction mixture was stirred at ambient temperature overnight. The resulting precipitate was isolated by filtration, washed with methanol and then dried to provide 42.1 g of $N^2$, $N^2$-bis(phenylmethyl)-3-nitroquinoline-2,4-diamine hydrochloride as a yellow solid.

Part C

Sodium borohydride (5.5 g, 0.147 mmole) was carefully added to a solution containing nickel (II) chloride hydrate (11.9 g, 0.05 mole) in methanol (1200 mL). $N^2$,$N^2$-bis(phenylmethyl)-3-nitroquinoline-2,4-diamine hydrochloride (42.1 g, 0.1 mole) was taken up in a mixture of methylene chloride (400 mL) and methanol (200 mL) and added to the nickel borate reagent. Additional sodium borohydride was carefully added until the generated foam was colorless. The reaction mixture was filtered through a layer of Celite™ filter agent. The filtrate was concentrated under vacuum. The residue was partitioned between methylene chloride and water. The methylene chloride layer was dried over magnesium sulfate then concentrated under vacuum. The residue was taken up in diethyl ether (about 1200 mL). Hydrochloric acid was bubbled through the ether solution for 5 minutes. The resulting precipitate was collected and dried to provide 32 g of $N^2$,$N^2$-bis(phenylmethyl)quinoline-2,3,4-triamine hydrochloride.

Part D

Triethylamine (3.6 mL, 25.6 mmole) was added to a suspension of $N^2$,$N^2$-bis(phenylmethyl)quinoline-2,3,4-triamine hydrochloride (5 g, 12.8 mmoles) in acetic acid (120 mL). Acetyl chloride (0.91 mL, 12.8 mmole) was added and the reaction mixture was heated at reflux for 5 to 6 hours then concentrated under vacuum. The residue was partitioned between diethyl ether and saturated aqueous sodium bicarbonate. The ether layer was dried then concentrated under vacuum. The residue was purified by column chromatography (silica gel eluting with methylene chloride containing 1–5% v/v ethyl acetate) to provide about 2.4 g of N,N-bis(phenylmethyl)-2-methyl-1H-imidazo[4,5-c]quinolin-4amine.

Part E

A suspension of sodium hydride (0.064 g, 2 mmole) in tetrahydrofuran (15 mL) was cooled in an ice bath. N,N-bis(phenylmethyl)-2-methyl-1H-imidazo[4,5-c]quinolin-4-amine (0.5 g, 1.32 mmole) was added and the reaction mixture was allowed to warm to room temperature for 20 minutes. Chloromethyl ethyl ether was added and the reaction mixture was stirred for 30 minutes. The reaction mixture was diluted with diethyl ether, washed twice with water, dried over magnesium sulfate and then concentrated under vacuum. The residue was purified by column chromatography (silica gel eluting with methylene chloride) to provide 0.43 g of N,N-bis(phenylmethyl)-1-ethoxymethyl-2-methyl-1H-imidazo[4,5-c]quinolin-4-amine.

Part F

Under a nitrogen atmosphere, a solution of N,N-bis(phenylmethyl)-1-ethoxymethyl-2-methyl- 1H-imidazo[4,5-c]quinolin-4-amine (1.12 g, 2.56 mmole) in tetrahydrofuran (20 mL) was cooled to −78° C. Butyllithium (1.03 mL of 2.5M in hexanes, 2.56 mmole) was added and the reaction mixture was stirred for 5 minutes. 1-Bromo-3-chloropropane (2.7 mL, 25 mmole) was added and the reaction mixture was allowed to warm to ambient temperature. When the reaction was complete, as indicated by thin layer chromatography (silica gel, 30% ethyl acetate in hexanes v/v), the reaction mixture was diluted with diethyl ether and water. The ether layer was separated, dried over magnesium sulfate and then concentrated under vacuum. The resulting residue was purified by column chromatography (silica gel eluting with 10–20% ethyl acetate in hexanes v/v) to provide 0.76 g of N,N-bis(phenylmethyl)-2-(4-chlorobutyl)-1-ethoxymethyl-1H-imidazo[ 4,5-c]quinolin-4-amine.

Part G

Methanol (several mL) was added to a suspension of N,N-bis(phenylmethyl)-2-(4-chlorobutyl)-1-ethoxymethyl-1H-imidazo[4,5-c]quinolin-4-amine (0.76 g, 1.5 mmole) in 3N hydrochloric acid (20 mL). The reaction mixture was heated on a stream bath for 4 hours then partitioned between methylene chloride and aqueous saturated sodium bicarbonate. The methylene chloride layer was separated, dried over magnesium sulfate and then concentrated under vacuum to provide 0.64 g of N,N-bis(phenylmethyl)-2-(4-chlorobutyl)-1H-imidazo[4,5-c]quinolin-4-amine.

Part H

Sodium iodide (1 g, 6 mmole) and potassium carbonate (0.8 g, 6 mmole) were added to a solution of N,N-bis(phenylmethyl)-2-(4-chlorobutyl)-1H-imidazo[4,5-c]quinolin-4-amine (0.55 g, 1.2 mmole) in acetone. The reaction mixture was heated at reflux for 4 hours, filtered, and then concentrated under vacuum. The residue was purified by flash chromatography (silica gel eluting with 10–15% ethyl acetate in hexanes v/v). Nuclear magnetic resonance spectroscopy indicated the possible presence of iodo intermediate; so the residue was taken up in acetone, combined with sodium iodide and potassium carbonate and heated at reflux over night. The reaction was worked up to provide 0.38 g of N,N-bis(phenylmethyl)-8,9,10,11 tetrahydropyrido-[ 1',2':1,2]imidazo[4,5-c]quinolin-4-amine.

Part I

Palladium hydroxide on carbon (0.35 g) was added to a solution of N,N-bis(phenylmethyl)-8,9,10,11 tetrahydropyrido[1',2':1,2]imidazo[4,5-c]quinolin-4-amine (0.38 g, 0.9 mmole) in formic acid (about 15 mL). The reaction mixture was heated at reflux for 3 days then diluted with methylene chloride and made basic (about pH 9) with 10% sodium hydroxide. The methylene chloride layer was separated, dried over magnesium sulfate and then concentrated under vacuum to provide a white solid. The material was purified by column chromatography (silica gel eluting with 4–10% methanol in methylene chloride v/v) to provide a solid. The solid was suspended in methylene chloride (20 mL) then isolated by filtration and dried to provide 70 mg of 8,9,10,11 tetrahydropyrido[1',2':1,2]imidazo[4,5-c]quinolin-4-amine as a solid, m.p. 275°–278° C. Calculated for $C_{14}H_{14}N_4$+0.2 $CH_2Cl_2$: %C, 66.81; %H, 5.69; %N, 21.95; Found: %C, 67.06; %H, 5.60; %N, 22.18.

EXAMPLE 2

10-Methyl-8,9,10,11-tetrahydropyrido[1',2',:1,2] imidazo[4,5-c]quinolin-6-amine Part A A solution of N,N-bis(phenylmethyl)-1-ethoxymethyl-2-methyl-1H-imidazo[4,5-c]quinolin-4-amine (1.8 g, 4.12 mmole, Example 1 Part E) in tetrahydrofuran (40 mL) was cooled to −78° C. Butyllithium (1.7 mL of 2.5M in hexanes, 4.2 mmole) was added and the reaction mixture was stirred for 20 minutes. 1-Bromo-3-chloro-2-methylpropane (4.8 mL, 41 mmole) was added and the reaction mixture was allowed to warm to ambient temperature over a period of 1 hour. The reaction mixture was diluted with diethyl ether and water. The ether layer was separated, dried over magnesium sulfate and then concentrated under vacuum. The resulting residue was purified by flash chromatography (silica gel eluting with 5–20% ethyl acetate in hexanes v/v) to provide 0.65 g of N,N-bis(phenylmethyl)-2-(4-chloro-3-methylbutyl)-1-ethoxymethyl-1H-imidazo[4,5-c]quinolin-4-amine.

Part B

Hydrochloric acid (80 mL of 6N) was added to a suspension of N,N-bis(phenylmethyl)-2-(4-chloro-3-methylbutyl)-1-ethoxymethyl-1H-imidazo[ 4,5-c]quinolin-4-amine (0.64 g, 1.2 mmole) in methanol (40 mL). The reaction mixture was heated at reflux for 2 hours (All of the methanol was driven off during this period.), diluted with methylene chloride and then made basic with 10% sodium hydroxide. The methylene chloride layer was separated, dried over magnesium sulfate and then concentrated to provide about 0.5 g of N,N-bis(phenylmethyl)-2-(4-chloro- 3-methylbutyl)-1H-imidazo[4,5-c]quinolin-4-amine.

Part C

A large excess (about 10 fold) of both sodium iodide and potassium carbonate were added to a solution of N,N-bis(phenylmethyl)-2-(4-chloro-3-methylbutyl)-1H-imidazo [4,5-c]quinolin-4-amine (about 0.5 g) in acetone (about 75 mL). The reaction mixture was heated at reflux overnight, diluted with additional acetone, filtered and then concentrated under vacuum. The residue was washed with methylene chloride to recover the product from salts then purified by column chromatography (silica gel eluting with 3% ethyl acetate in methylene chloride v/v) to provide 0.35 g of N,N-bis(phenylmethyl)-8,9,10,11 tetrahydro-10-methylpyrido[ 1',2':1,2]imidazo[4,5-c]quinolin-4-amine.

Part D

Palladium hydroxide on carbon (0.35 g) was added to a solution of N,N-bis(phenylmethyl)-8,9,10,11 tetrahydro-10-methylpyrido[1',2':1,2]imidazo[4,5-c]quinolin-4-amine (0.35 g, 0.809 mmole) in formic acid (about 15 mL). The reaction mixture was heated at reflux for 3 days, diluted with a mixture of methanol and water, and then filtered through Celite™ filter agent. The filtrate was concentrated under vacuum and then made basic with 10% sodium hydroxide. The resulting precipitate was isolated by filtration then purified by column chromatography (silica gel eluting with 2–5% methanol in methylene chloride v/v) to provide 0.1 g of 10-methyl-8,9,10,11-tetrahydropyrido[ 1',2',:1,2]imidazo [4,5-c]quinolin-6-amine as a solid, m.p. 279°–281° C. Calculated for $C_{15}H_{16}N_4$: %C, 71.40; %H, 6.39; %N, 22.20; Found: %C, 71.10; %H, 6.46; %N, 22.25.

EXAMPLE 3

8H-9,10,11,12-Tetrahydrohexamethyleneimino[1',2':1,2] imidazo[4,5,-c]quinolin-6-amine Hydrate Part A A solution of N,N-bis(phenylmethyl)-1-ethoxymethyl-2-methyl-1H-imidazo[4,5-c]quinolin-4-amine (1.5 g, 3.43 mmole, Example 1 Part E) in tetrahydrofuran (30 mL) was cooled to −78° C. Butyllithium (1.4 mL of 2.5M in hexanes, 3.5 mmole) was added dropwise followed by the addition of 1-bromo-4-chlorobutane (4 mL, 34 mmole). The reaction mixture was allowed to warm to ambient temperature then it was quenched with diethyl ether and water. The ether layer was separated, dried over magnesium sulfate and then concentrated under vacuum. The resulting residue was purified by column chromatography (silica gel eluting with 10% ethyl acetate in hexanes v/v) to provide 1.5 g of N,N- bis(phenylmethyl)-2-(5-chloropentyl)-1-ethoxymethyl-1H-imidazo[4,5-c]quinolin-4-amine.

Part B

A suspension of N,N-bis(phenylmethyl)-2-(5-chloropentyl)-1-ethoxymethyl-1H-imidazo[ 4,5-c]quinolin-4-amine (1.5 g, 3 mmole) in 6N hydrochloric acid (100 mL) was heated at reflux for 1 hour. The reaction mixture was cooled, diluted with methylene chloride, made basic with 10% sodium hydroxide and then extracted with methylene chloride (400 mL total). The methylene chloride extracts were combined, dried over magnesium sulfate and then concentrated under vacuum to provide about 1.3 g of N,N-bis(phenylmethyl)-2-(5-chloropentyl)-1H-imidazo[4,5-c]quinolin-4-amine.

Part C

Using the method of Example 2 Part C, N,N-bis(phenylmethyl)-2-(5-chloropentyl)- 1H-imidazo[4,5-c]quinolin-4-amine (1.3 g, 3 mmole) was cyclized to provide 1.1 g of N,N-bis(phenylmethyl)-8H-9,10,11,12-tetrahydrohexamethyleneimino[ 1',2':1,2]imidazo[4,5-c]quinolin-6-amine as a white solid.

Part D

Palladium hydroxide on carbon (1 g) was added to a solution of N,N-bis(phenylmethyl)-8H-9,10,11,12-tetrahydrohexamethyleneimino[ 1',2':1,2]imidazo[4,5-c]quinolin-6-amine (1 g, 2.3 mmole) in formic acid (about 30 mL). The reaction mixture was heated at reflux for 4 days, filtered, washed with methanol/methylene chloride and then concentrated under vacuum. The residue was partitioned between methylene chloride and 10% sodium hydroxide. The methylene chloride layer was separated, dried over magnesium sulfate and then concentrated under vacuum. The residue was purified by column chromatography (silica gel eluting with 3–10% methanol in methylene chloride v/v) to provide 0.4 g of 8H-9,10,11,12-tetrahydrohexamethyleneimino[ 1',2':1,2]imidazo[4,5-c]quinolin-6-amine hydrate as a white solid, m.p. 237°–240° C. Calculated for $C_{15}H_{16}N_4+\frac{1}{3}H_2O$: %C, 69.74; %H, 6.50; %N, 21.69; Found: %C, 69.74; %H, 6.27; %N, 21.37.

EXAMPLE 4

9,10-Dihydro-8H-pyrrolo[1',2':1,2] imidazo[4,5,-c]quinolin-4-amine Hydrate

Part A

A solution of N,N-bis(phenylmethyl)-1-ethoxymethyl-2-methyl-1H-imidazo[4,5-c]quinolin-4-amine (1.7 g, 3.9 mmole, Example 1 Part E) in tetrahydrofuran (50 mL) was cooled to −78° C. Butyllithium (1.6 mL of 2.5M in hexanes, 4.1 mmole) was added dropwise and the reaction mixture was stirred for 5 minutes. Ethylene oxide was run over the surface of the reaction mixture. After 10 minutes the reaction mixture was allowed to warm to ambient temperature. The ethylene oxide addition was stopped when the reaction temperature reached 0° C. The reaction was quenched with diethyl ether and water. The ether layer was separated, dried over magnesium sulfate and then concentrated under vacuum. The resulting residue was purified by column chromatography (silica gel eluting with 5–10% ethyl acetate in methylene chloride v/v) to provide 1.4 g of N,N-bis(phenylmethyl)-2-(3-hydroxypropyl)-1-ethoxymethyl-1H-imidazo[4,5-c]quinolin-4-amine.

Part B

Thionyl chloride (5 mL, 68 mmole) was added to N,N-bis(phenylmethyl)-2-(3-hydroxypropyl)-1-ethoxymethyl-1H-imidazo[4,5-c]quinolin-4-amine (1 g, 2.1 mmole) and the reaction mixture was stirred rapidly until thin layer chromatography (silica gel, 10% ethyl acetate in methylene chloride v/v) indicated that the reaction was complete. The reaction mixture was diluted with methylene chloride then neutralized with 10% sodium hydroxide and sodium bicarbonate. The methylene chloride layer was separated, dried over magnesium sulfate and then concentrated under vacuum. The residue was purified by column chromatography (silica gel eluting with 10–30% ethyl acetate in hexanes v/v) to provide 1 g of N,N-bis(phenylmethyl)-2-( 3-chloropropyl)-1-ethoxymethyl-1H-imidazo[4,5-c]quinolin-4-amine.

Part C

A suspension of N,N-bis(phenylmethyl)-2-(3-chloropropyl)-1-ethoxymethyl- 1H-imidazo[4,5-c]quinolin-4-amine (1 g, 2.0 mmole) in 6N hydrochloric acid (80 mL) was heated at reflux for 2 hours and then stirred at ambient temperature overnight. The reaction mixture was neutralized with 10% sodium hydroxide then extracted with methylene chloride. The extract was dried over magnesium sulfate then concentrated under vacuum to provide 0.8 g of N,N-bis(phenylmethyl)-2-(3-chloropropyl)-1H-imidazo[4,5-c]quinolin-4-amine.

Part D

Potassium carbonate (10X excess) and sodium iodide (5X excess) were added to a solution of N,N-bis(phenylmethyl)-2-(3-chloropropyl)- 1H-imidazo[4,5-c]quinolin-4-amine (0.8 g, 1.8 mmole) in acetone. The reaction was heated at reflux for 2 hours, filtered and then concentrated under vacuum. The residue was partitioned between methylene chloride and water. The methylene chloride layer was separated, dried over magnesium sulfate and then concentrated under vacuum. The residue was purified by column chromatography (silica gel eluting with 10–30% ethyl acetate in hexanes v/v) to provide 0.25 g of N,N-bis(phenylmethyl)-9,10-dihydro- 8H-pyrrolo[ 1',2':1,2]imidazo[4,5-c]quinolin-4-amine.

Part E

Palladium hydroxide on carbon (0.5 g) was added to a solution of N,N-bis(phenylmethyl)-9,10-dihydro-8H-pyrrolo[ 1',2':1,2]imidazo[4,5-c]quinolin-4-amine (0.25 g, 0.62 mmole) in formic acid (75 mL). The reaction mixture was heated at reflux for 4 days then diluted with methanol and filtered. The filtrate was concentrated under vacuum then mixed with water and sodium bicarbonate. A gray precipitate was isolated by filtration. The filtrate was concentrated. The resulting residue was slurried with a mixture of methanol and methylene chloride and then filtered. The filtrate was combined with the previously isolated gray precipitate then purified by column chromatography (silica gel eluting with 3–5% methanol in methylene chloride v/v) to provide 80 mg of N,N- bis(phenylmethyl)-9,10-dihydro-8H-pyrrolo[ 1',2':1,2]imidazo[4,5-c]quinolin-4-amine as a white solid, m.p. 275°–277° C. Analysis: Calculated for $C_{13}H_{12}N_4+\frac{1}{3}H_2O$: %C, 67.81; %H, 5.54; %N, 24.33; Found: C, 67.80; %H, 5.26; %N, 24.28.

EXAMPLE 5

10,11-Dihydro-8H-[1,4]-oxazino[4',3':1,2] imidazo[4,5-c]quinolin-6-amine

Part A

A suspension of $N^2,N^2$-bis(phenylmethyl)quinoline-2,3,4-triamine hydrochloride (10 g, 25.6 mmole, Example 1 Part C) in triethyl orthoformate (40 mL) was heated at about 120° C. for 30 minutes, cooled to ambient temperature and then diluted with diethyl ether. The resulting precipitate was isolated by filtration then partitioned between ammonium hydroxide and methylene chloride. The methylene chloride layer was separated, washed twice with water, dried over magnesium sulfate and then concentrated under vacuum to provide 8.6 g of N,N-bis(phenylmethyl)-1H-imidazo[4,5-c]quinolin-4-amine as a dark brown solid.

Part B

A solution of N,N-bis(phenylmethyl)-1H-imidazo[4,5-c]quinolin-4-amine (2 g, 5.49 mmole) in tetrahydrofuran (10 mL) was added to a suspension of sodium hydride (0.21 g, 6.58 mmole) in tetrahydrofuran (25 mL). After 30 minutes chloromethyl ethyl ether (0.61 mL, 6.58 mmole) was added and the reaction mixture was stirred for 2 hours. The reaction mixture was diluted with diethyl ether, washed with water, dried over magnesium sulfate, and then concentrated under vacuum to provide crude product as a brown oil. The oil was purified by column chromatography (silica gel eluting with 20–30% ethyl acetate in hexanes v/v) to provide 1.77 g of N,N-bis(phenylmethyl)-1-ethoxymethyl-1H-imidazo[4,5-c]quinolin-4-amine as a white/tan solid.

Part C

Butyllithium (1.6 mL of 2.5M in hexanes, 4 mmole) was added to a chilled (dry ice/acetone bath) solution of N,N-bis(phenylmethyl)-1-ethoxymethyl-1H-imidazo[4,5-c]quinolin-4-amine (1.7 g, 4 mmole) in tetrahydrofuran. No color change was observed. The reaction mixture was warmed to −20° C. (dry ice/carbon tetrachloride) and the reaction turned red in color. Formaldehyde gas entrained in a flow of nitrogen was added to the reaction mixture. After several minutes the reaction turned to a solid mass and the ice bath was removed. The reaction mixture was allowed to warm to ambient temperature and the color of the reaction mixture changed from red to yellow. The reaction was diluted with diethyl ether and water. The ether layer was separated, dried over magnesium sulfate and then concentrated under vacuum. The residue was purified by column chromatography (silica gel eluting with 10–20% ethyl acetate in hexanes v/v) to provide 1 g of 4-bis(phenylmethyl)amino-1-ethoxymethyl- 1H-imidazo[4,5-c]quinolin-2-methanol.

Part D

Sodium hydride (0.11 g, 3.3 mmole) was added to a solution of 4-bis(phenylmethyl)amino-1-ethoxymethyl-1H-imidazo[4,5-c]quinolin-2-methanol (1 g, 2.21 mmole) in N,N-dimethylformamide (15 mL) and the resulting mixture was stirred for 10 minutes. 1-Bromo-2-(trityloxy)ethane was added and stirring was continued at ambient temperature for 3–4 hours. The reaction was quenched with diethyl ether and water. The ether layer was separated, washed several times with water, dried over magnesium sulfate and then concentrated under vacuum. The residue was purified by column chromatography (silica gel eluting with 10–30% ethyl acetate in hexanes v/v) to provide 1.1 g of N,N-bis(phenylmethyl)-1-ethoxymethyl-2-[ (2-triphenylmethoxy)ethoxy] methyl-1H-imidazo[4,5-c]quinolin-4-amine.

Part E

A suspension of N,N-bis(phenylmethyl)-1-ethoxymethyl-2-[(2-triphenylmethoxy)ethoxy] methyl-1H-imidazo[4,5-c]quinolin-4-amine (1.1 g, 1.5 mmole) in 6N hydrochloric acid (25 mL) was heated on a steam bath for 1.5 hours. The reaction mixture was neutralized to pH 7 then extracted with methylene chloride. The extract was dried then concentrated under vacuum. The residue was purified by column chromatography (silica gel eluting with 10–50% ethyl acetate in hexanes v/v) to provide 0.5 g of N,N-bis(phenylmethyl)-2-(2-hydroxyethoxy)methyl-1H-imidazo[4,5-c]quinolin-4-amine.

Part F

Triethylamine (0.17 mL, 1.25 mmole) was added to a solution of N,N-bis(phenylmethyl)-2-(2-hydroxyethoxy)methyl-1H-imidazo[4,5-c]quinolin-4-amine (0.5 g, 1.14 mmole) in methylene chloride (20 mL). Methanesulfonyl chloride (0.09 mL, 1.14 mmole) was added and the reaction mixture was stirred at ambient temperature for 1 hour. The reaction mixture was diluted with methylene chloride, washed with water, dried over magnesium sulfate and then concentrated under vacuum to provide 0.6 g of N,N-bis(phenylmethyl)-2-(2-methylsulfonyloxyethoxy)methyl- 1H-imidazo[4,5-c]quinolin-4-amine.

Part G

Excess potassium carbonate and excess sodium iodide were added to a solution of N,N-bis(phenylmethyl)-2-(2-methylsulfonyloxyethoxy)methyl- 1H-imidazo[4,5-c]quinolin-4-amine (0.6 g, 1.14 mmole) in acetone (200 mL). The reaction mixture was heated at reflux overnight then concentrated under vacuum. The residue was partitioned between methylene chloride (150 mL) and water (50 mL). The methylene chloride was separated, dried over magnesium sulfate and then concentrated under vacuum. The residue was purified by column chromatography (silica gel eluting with 10:10:80 v/v/v methylene chloride:ethyl acetate:hexanes) to provide 0.42 g of N,N-bis(phenylmethyl)-10,11-dihydro- 8H-[1,4]-oxazino[4',3':1,2]imidazo[4,5-c]quinolin-6amine as a white solid.

Part H

Palladium hydroxide on carbon (0.5 g) was added to a solution of N,N-bis(phenylmethyl)-10,11-dihydro-8H-[ 1,4]-oxazino[4',3':1,2]imidazo[4,5-c]quinolin-6-amine (0.4 g, 0.95 mmole) in formic acid (about 40 mL). The reaction mixture was heated at reflux for 6 days then diluted with methanol and filtered through a layer of Celite™ filter agent. The filtrate was made basic with ammonium hydroxide then concentrated under vacuum. The residue was taken up in a mixture of methanol and methylene chloride. Silica gel was added and the resulting mixture was concentrated under vacuum. The solid was placed on a column and eluted with 2–5% methanol in methylene chloride to provide a white solid. The nuclear magnetic resonance spectra was consistent with the formate salt of the desired product. The salt was taken up in 5% hydrochloric acid and heated on a steam bath for 30 minutes. The mixture was made basic with 10% sodium hydroxide. The resulting precipitate was isolated by filtration, washed with water and dried under vacuum to provide 75 mg of 10,11-dihydro-8H-[1,4]-oxazino[4',3':1,2]imidazo[4,5-c]quinolin-6-amine as a solid, m.p. 258°–259° C. Analysis: Calculated for $C_{13}H_{12}N_4O$: %C, 64.99; %H, 5.03; %N, 23.32; Found: %C, 64.61; %H, 4.88; %N, 23.18.

INTERFERON (α) INDUCTION IN HUMAN CELLS

An in vitro human blood cell system was used to assess interferon induction by compounds of the invention. Activity is based on the measurement of interferon secreted into culture media. Interferon is measured by bioassay.

Blood Cell Preparation for Culture

Whole blood is collected by venipuncture into EDTA vacutainer tubes. Peripheral blood mononuclear cells (PBM's) are separated from whole blood by using either LeucoPREP™ Brand Cell Separation Tubes (available from Becton Dickinson) or Ficoll-Paque® solution (available from Pharmacia LKB Biotechnology Inc, Piscataway, N.J.). The PBM's are suspended at $1\times10^6$/mL in RPMI 1640 media (available from GIBCO, Grand Island, N.Y.) containing 25 mM HEPES (N-2-hydroxyethylpiperazine-N'-2-ethanesulfonic acid) and L-glutamine (1% penicillin-streptomycin solution added) with 10% heat inactivated (56° C. for 30 minutes) autologous serum added. 200 μL portions of PBM suspension are added to 96 well (flat bottom) MicroTest III sterile tissue culture plates.

Compound Preparation

The compounds are solubilized in ethanol, dimethyl sulfoxide or tissue culture water then diluted with tissue culture water, 0.01N sodium hydroxide or 0.01N hydrochloric acid (The choice of solvent will depend on the chemical characteristics of the compound being tested.). Ethanol or DMSO concentration should not exceed a final concentration of 1% for addition to the culture wells. Compounds are initially tested in a concentration range of from about 0.1 μg/mL to about 5 μg/mL. Compounds which show induction at a concentration of 0.5 μg/mL are then tested in a wider concentration range.

Incubation

The solution of test compound is added in a volume (less than or equal to 50 μL) to the wells containing 200 μL of diluted whole blood or of PBM's in media. Solvent and/or media is added to control wells (wells with no test compound) and as needed to adjust the final volume of each well to 250 μL. The plates are covered with plastic lids, vortexed gently and then incubated for 48 hours at 37° C. with a 5% carbon dioxide atmosphere.

Separation

Following incubation, the plates are covered with parafilm and then centrifuged at 1000 rpm for 10 to 15 minutes at 4° C. in a Damon IEC Model CRU-5000 centrifuge. Media (about 200 μL) is removed from 4 to 8 wells and pooled into 2 mL sterile freezing vials. Samples are maintained at −70° C. until analysis.

Interferon Analysis/Calculation

Interferon is determined by bioassay using A549 human lung carcinoma cells challenged with encephalomyocarditis. The details of the bioassay method have been described by G. L. Brennan and L. H. Kronenberg in "Automated Bioassay of Interferons in Micro-test Plates", Biotechniques, June/July, 78, 1983, incorporated herein by reference. Briefly stated the method is as follows: interferon dilutions and A549 cells are incubated at 37° C. for 12 to 24 hours. The incubated cells are infected with an inoculum of encephalomyocarditis virus. The infected cells are incubated for an additional period at 37° C. before quantifying for viral cytopathic effect. The viral cytopathic effect is quantified by staining followed by spectrophotometric absorbance measurements. Results are expressed as alpha reference units/mL based on the value obtained for NIH HU IF-L standard. The interferon was identified as essentially all interferon alpha by testing in checkerboard neutralization assays against rabbit anti-human interferon (beta) and goat anti-human interferon (alpha) using A549 cell monolayers challenged with encephalomyocarditis virus. Results are shown in the table below wherein the absence of an entry indicates that the compound was not tested at that particular dose concentration.

Interferon (α) Induction in Human Cells

| Compound of Example | α Reference Units/mL Dose Concentration (μg/mL) 0.01 | 0.05 | 0.10 | 0.50 | 1.0 | 5.0 |
|---|---|---|---|---|---|---|
| 1 | 2 | 5 | 320 | 1000 | 370 | 46 |
| 2 | — | — | 4 | 50 | 66 | 7 |
| 3 | — | — | 4 | 100 | 130 | 32 |
| 4 | 5 | 510 | 1200 | 160 | 190 | 380 |
| 5 | 1 | 1 | 510 | 310 | 170 | 210 |

INTERFERON INDUCTION IN MICE

This test method was used to assess the ability of compounds of the invention to induce interferon biosynthesis in mice.

For each dose level being tested, three groups (three mice per group) of male mice (nonfasted) are dosed orally with compound. One hour later blood is collected from the retrobulbar plexus and pooled. The blood is centrifuged and serum collected and aliquoted. The serum samples are stored frozen at −70° C. until analysis. This procedure is repeated at 2 hours post dose with the second group of mice and at four hours post dose with the third group of mice.

Samples are assayed as described above in connection with the analysis of interferon induction in human cells. The results are expressed in the table below as α/β reference units/mL based on the value obtained for a mouse MU-1-IF standard. Results are shown in the table below wherein results designated "<" a certain number indicate that interferon was not detectable in amounts above the lower sensitivity level of the assay.

Interferon Induction in Mice

| Compound of Example | Dose (mg/Kg) | Reference Units/mL 1 hr | 2 hr | 4 hr |
|---|---|---|---|---|
| 1 | 0.3 | <250 | <250 | <250 |
| 1 | 1.0 | 480 | 480 | <250 |
| 1 | 3.0 | 480 | 1300 | 330 |
| 1 | 10.0 | 1600 | 4300 | 480 |
| 3 | 0.3 | <380 | <380 | <380 |
| 3 | 1.0 | <380 | <380 | <380 |
| 3 | 3.0 | 1100 | 820 | <380 |
| 3 | 10.0 | 1500 | 2900 | 660 |
| 4 | 0.3 | <520 | 520 | <520 |
| 4 | 1.0 | 1100 | 1100 | <520 |
| 4 | 3.0 | 2700 | 3500 | <520 |
| 4 | 10.0 | 4700 | 11000 | <520 |
| 5 | 0.3 | <310 | <310 | <310 |
| 5 | 1.0 | 310 | <310 | <310 |
| 5 | 3.0 | 1100 | 1200 | 310 |
| 5 | 10.0 | 1700 | 2100 | 630 |

INDIRECT IN-VITRO ANTIVIRAL ACTIVITY

The test method described below demonstrates the ability of compounds of the invention to inhibit the progress of viral infection.

Whole blood is collected by venipuncture into EDTA vacutainer tubes. Peripheral blood mononuclear cells (PBM's) are isolated using Ficoll-Paque® solution (available from Pharmacia LKB Biotechnology Inc., Piscataway, N.J.). The PBM's are washed with phosphate buffer saline then diluted with RPMI 1640 medium (available from GIBCO, Grand Island, N.Y.) and 10% fetal bovine serum to obtain a final concentration of $2.5\times10^6$ cells/mL. One mL portions of PBM's in medium are placed in 15 mL polypropylene tubes. The test compound is dissolved in dimethyl sulfoxide then diluted with RPMI 1640 medium. The solution of test compound is added to the tubes containing the PBM's to give final concentrations ranging from 0.05 μg/mL to 1.0 μg/mL. Control tubes do not receive any test compound. The tubes are then incubated for 24 hours at 37° C. with a 5% carbon dioxide atmosphere. Following incubation the tubes are centrifuged at 400 xg for 5 minutes. The supernatant is removed. The PBM's are brought up in 100 μL of RPMI 1640 medium and then infected with a 100 μL containing $10^5$ tissue culture 50% infectious doses of vesicular stomatitis virus (VSV). The tubes are incubated for 30 minutes at 37° C. to allow virus adsorption. One mL of RPMI 1640 medium is added to each tube and the tubes are incubated for 48 hours at 37° C. The tubes are frozen then thawed to lyse the cells. The tubes are centrifuged at 400 xg for 5 minutes to remove cellular debris then the supernatant is assayed by serial tenfold dilutions on Vero cells in 96 well microtiter plates. The infected cells are incubated for 24 hours at 37° C. before quantifying for viral cytopathic effect. The viral cytopathic effect is quantified by staining with 0.05% crystal violet. Results are presented as VSV inhibition, defined as the $\log_{10}$ (control VSV yield/experimental VSV yield). Results are shown in the table below wherein the absence of an entry indicates that the compound was not tested at that particular concentration. Control tubes have a value of 0.

In-vitro Antiviral Activity

| Compound of Example | VSV Yield Inhibition Dose Concentration (μg/mL) 0.05 | 0.1 | 0.5 | 1.0 |
|---|---|---|---|---|
| 1 | 8.0 | 8.0 | 8.0 | — |
| 2 | — | 2.0 | 4.0 | 5.0 |

The claimed invention is:

1. A compound of Formula II

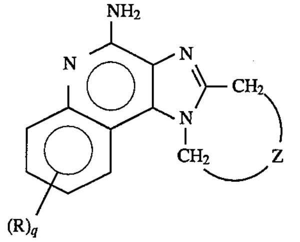

II wherein Z is selected from the group consisting of:

$-(CH_2)_n-$ wherein n is 1 to 4;

$-(CH_2)_a-C(R_1R_2)(CH_2)_b-$, wherein a and b are integers and a+b is 0 to 3, $R_1$ is hydrogen or alkyl of 1 to 4 carbon atoms, and $R_2$ is selected from the group consisting of alkyl of 1 to 4 carbon atoms, hydroxy, $-OR_3$ wherein $R_3$ is alkyl of 1 to 4 carbon atoms, and $-NR_4R'_4$ wherein $R_4$ and $R'_4$ are independently hydrogen or alkyl of 1 to 4 carbon atoms; and $-(CH_2)_a-(Y)-(CH_2)_b-$ wherein a and b are integers and a+b is 0 to 3, and Y is O, S, or $-NR_5-$ wherein $R_5$ is hydrogen or alkyl of 1 to 4 carbon atoms;

and wherein q is 0 or 1 and R is selected from the group consisting of alkyl of 1 to 4 carbon atoms, alkoxy of 1 to 4 carbon atoms, and halogen, and pharmaceutically acceptable salts thereof.

2. A compound according to claim 1, wherein Z is $-(CH_2)_n-$ and n is 1 to 4, and pharmaceutically acceptable salts thereof.

3. A compound according to claim 2, wherein n is 1, 2, or 3, and pharmaceutically acceptable salts thereof.

4. A compound according to claim 1 wherein Z is $-(CH_2)_a-C(R_1R_2)(CH_2)_b-$ wherein a and b are integers and a+b is 0 to 3, $R_1$ is hydrogen or alkyl of 1 to 4 carbon atoms, and $R_2$ is selected from the group consisting of alkyl of 1 to 4 carbon atoms, hydroxy, $-OR_3$ wherein $R_3$ is alkyl of 1 to 4 carbon atoms, and $-NR_4R'_4$ wherein $R_4$ and $R'_4$ are independently hydrogen or alkyl of 1 to 4 carbon atoms, and pharmaceutically acceptable salts thereof.

5. A compound according to claim 4, wherein $R_1$ is hydrogen and $R_2$ is alkyl of 1 to 4 carbon atoms, and pharmaceutically acceptable salts thereof.

6. A compound according to claim 5, wherein $R_2$ is methyl, and pharmaceutically acceptable salts thereof.

7. A compound according to claim 1, wherein Z is $-(CH_2)_a-(Y)-(CH_2)_b-$ wherein a and b are integers and a+b is 0 to 3, and Y is O, S, or $-NR_5-$ wherein $R_5$ is hydrogen or alkyl of 1 to 4 carbon atoms, and pharmaceutically acceptable salts thereof.

8. A compound according to claim 7, wherein Y is O, and pharmaceutically acceptable salts thereof.

9. A compound according to claim 8, wherein a+b is 1, and pharmaceutically acceptable salts thereof.

10. A compound according to claim 1, selected from the group consisting of:

8,9,10,11-tetrahydropyrido[1',2':1,2] imidazo[4,5-c]quinolin-6-amine, 10-methyl-8,9,10,11-tetrahydropyrido[1',2',:1,2] imidazo[4,5-c]quinolin-6-amine, 8H-9,10,11,12-tetrahydrohexamethyleneimino[ 1',2':1,2] imidazo[4,5-c]quinolin-6-amine, 9,10-dihydro-8H-pyrrolo[1',2':1,2]imidazo[4,5-c] quinolin-4-amine, 10,11-dihydro-8H-[1,4]-oxazino[4',3':1,2] imidazo[4,5-c] quinolin-6-amine, and pharmaceutically acceptable salts thereof.

11. A pharmaceutical formulation comprising: (i) a compound according to claim 1 in an amount effective to induce interferon biosynthesis in an animal, and (ii) a pharmaceutically acceptable vehicle.

12. A method of inducing interferon biosynthesis in an animal, comprising the step of administering to said animal a compound according to claim 1 in an amount effective to induce said interferon biosynthesis.

* * * * *